(12) United States Patent
Uematsu

(10) Patent No.: US 7,659,528 B2
(45) Date of Patent: Feb. 9, 2010

(54) PARTICLE BEAM IRRADIATION SYSTEM

(75) Inventor: Minoru Uematsu, 651 Yamanouchi, Kamakura-shi, Kanagawa-ken (JP)

(73) Assignees: Minoru Uematsu, Kamakura-shi (JP); Masayuki Atsuchi, Kagoshima-shi (JP); James Robert Wong, Morristown, NJ (US)

( * ) Notice: Subject to any disclaimer, the term of this patent is extended or adjusted under 35 U.S.C. 154(b) by 195 days.

(21) Appl. No.: 11/896,090

(22) Filed: Aug. 29, 2007

(65) Prior Publication Data

US 2008/0197296 A1 Aug. 21, 2008

(30) Foreign Application Priority Data

Feb. 20, 2007 (JP) .............................. 2007-039359

(51) Int. Cl.
*H05G 1/02* (2006.01)
*A61N 5/00* (2006.01)

(52) U.S. Cl. .................. 250/493.1; 250/495.1; 600/407; 600/427; 378/20; 378/37; 378/65; 378/197

(58) Field of Classification Search ....................... None
See application file for complete search history.

(56) References Cited

U.S. PATENT DOCUMENTS

| | | | | |
|---|---|---|---|---|
| 4,726,046 A | * | 2/1988 | Nunan | 378/65 |
| 5,117,829 A | * | 6/1992 | Miller et al. | 600/427 |
| 5,329,567 A | * | 7/1994 | Ikebe | 378/20 |
| 5,912,943 A | * | 6/1999 | Deucher et al. | 378/98.8 |
| 6,007,243 A | * | 12/1999 | Ergun et al. | 378/197 |
| 6,094,760 A | | 8/2000 | Nonaka et al. | |
| 6,205,347 B1 | * | 3/2001 | Morgan et al. | 600/407 |
| 6,666,579 B2 | * | 12/2003 | Jensen | 378/197 |
| 7,173,265 B2 | * | 2/2007 | Miller et al. | 250/492.3 |
| 7,199,382 B2 | * | 4/2007 | Rigney et al. | 250/492.1 |

(Continued)

FOREIGN PATENT DOCUMENTS

EP 1 683 545 A2 7/2006

(Continued)

OTHER PUBLICATIONS

T. Kamada et al., "A horizontal CT system dedicated to heavy-ion beam treatment", *Radiotherapy and Oncology*, Elsevier, vol. 50, No. 2, (Feb. 1999) pp. 235-237.

*Primary Examiner*—David A Vanore
(74) *Attorney, Agent, or Firm*—Birch, Stewart, Kolasch & Birch, LLP

(57) ABSTRACT

A particle beam irradiation system includes a particle beam irradiation apparatus, which is free of a gantry structure, having a particle beam irradiator for irradiating an affected area of a patient with a particle beam, the particle beam irradiator being housed in a chamber, a CT scanner installed in the chamber, for positionally confirming the affected area of the patient, a drive unit for moving the patient from a detection range to an irradiation range, a patient fixing device for fixing the patient in position, the device being mounted on the drive unit for rotation, and a housing unit having a structure housing the drive unit with the patient fixing device mounted and the CT scanner, the housing unit being rotatable about an axis perpendicular to a plane including a direction in which the particle beam is applied and a direction in which the drive unit moves.

13 Claims, 3 Drawing Sheets

U.S. PATENT DOCUMENTS 7,425,717 B2 * 9/2008 Matsuda et al. .......... 250/492.3
2004/0034438 A1 * 2/2004 Uematsu ..................... 700/59

FOREIGN PATENT DOCUMENTS

| JP | 9-192244 A | 7/1997 |
| JP | 2003-190304 A | 7/2003 |
| JP | 2006-218315 A | 8/2006 |
| WO | WO-2005/018734 A2 | 3/2005 |

* cited by examiner

PARTICLE BEAM IRRADIATION SYSTEM

BACKGROUND OF THE INVENTION

1. Field of the Invention

The present invention relates to a particle beam irradiation system for accurately irradiating the affected area of a patient with a particle beam such as a proton beam, a heavy ion beam, or the like, or more particularly to a particle beam irradiation system having a particle beam irradiation apparatus which is free of a rotating gantry structure and which radiates a particle beam from one direction, so that the particle beam irradiation system can be reduced in overall size and cost, and the particle beam irradiation apparatus has its accuracy control made easy. The particle beam irradiation system according to an embodiment of the present invention has a unit structure housing a CT scanner and a drive unit in integral combination, the CT scanner being installed in a treatment chamber for accurately confirming the position of the affected area of the patient and the drive unit being integrally combined with the CT scanner for moving the patient from the CT scanner to a particle beam irradiation range. For treating the patient with the particle beam irradiation system, the particle beam irradiation system employs a fixing device for fixing the patient to the drive unit, the fixing device being rotatable about the craniocaudal axis of the patient which is being fixed to the drive unit by the fixing device. Accordingly, the present invention is concerned with a particle beam irradiation system for setting the patient's body to any of various angles, detecting the affected area of the patient with a CT scanner, and moving a drive unit while the patient is being held in a set posture, for thereby accurately bringing the affected area of the patient into a particle beam applying position. The particle beam irradiation system according to an embodiment of the present invention has a unit structure housing a CT scanner and a drive unit in integral combination, the unit structure being rotatable about an axis perpendicular to a plane which includes both the direction in which the particle beam is applied and the direction which the drive unit moves, while the patient is being held in a constant posture. Consequently, the present invention relates to a particle beam irradiation system for accurately aiming at the affected area of the patient from many directions in a three-dimensional space with respect to one direction in which the particle beam is applied.

2. Description of the Related Art

Heretofore, there has been known a process of treating a cancer or the like by irradiating the affected area of the patient with a particle beam (ion beam) such as a proton beam, a heavy ion beam, or the like. The particle radiation therapy is capable of applying a lower radiation dose to a normal tissue than the radiation therapy in the past based on a peculiar dose distribution of the particle beam. For further reducing a redundant radiation dose of the radiation beam applied to a normal tissue, there has been employed a rotary gantry structure for applying the particle beam at an appropriate angle to the patient's body (multiple field irradiation). For example, Japanese Patent Laid-open No. 2006-218315 (hereinafter referred to as Patent Document 1) discloses a medical particle beam irradiation apparatus including a charged particle beam generator having an ion source, a preaccelerator, and a synchrotron, and a rotary gantry. Japanese Patent Laid-open No. 2003-190304 discloses a particle beam treatment apparatus for treating the affected area of a patient by irradiating it with a charged particle beam such as a proton beam, a heavy ion beam, or the like. The disclosed particle beam treatment apparatus has a treatment table for placing the patient thereon, the treatment table having a top plate with a recess defined therein. When the patient on the treatment table is irradiated with the particle beam applied from below by a rotary gantry, the particle beam is directly applied to the patient's body through the recess, not through the top plate.

Japanese Patent laid-open No. Hei 9-192244 (hereinafter referred to as Patent Document 3) reveals a particle beam irradiation apparatus having a particle beam generating means for generating a particle beam such as a proton beam, a particle beam circularly accelerating means for applying a magnetic field to the generated particle beam to emit the particle beam which has been rotated in a circular pattern and accelerated, a beam transporting means for transporting the particle beam to an irradiation chamber where an object to be irradiated is placed, an irradiation field forming means for shaping the particle beam into a desired shape and applying the shaped particle beam to the object, and a rotating means for rotating the particle beam circularly accelerating means, the beam transporting means, and the irradiation field forming means in unison with each other. The particle beam circularly accelerating means has an acceleration trajectory plane lying perpendicularly to the axis of rotation of the rotating means. The object to be irradiated with the particle beam is disposed on the axis of rotation of the rotating means. Patent Document 3 also discloses a rotary particle beam irradiation apparatus in the past having a cyclotron as a particle beam circularly accelerating means for generating a particle beam such as a proton beam and accelerating the particle beam to a high energy level, a quadrupole electromagnet for focusing the particle beam, which is a cluster of particles, into a desired shape, a deflection electromagnet for deflecting the particle beam, a directional control electromagnet for changing the direction in which the particle beam is transported, and a rotary particle beam irradiation table assembly for applying the particle beam to a target which is a cancer patient. The rotary particle beam irradiation table assembly includes a treatment table disposed at the rotational center, a beam transporting means for deflecting the particle beam at a right angle and guiding the particle beam between a pair of rotating frames in order to apply the particle beam perpendicularly to the target placed on the treatment table, and an irradiation field forming means for forming an irradiation field in alignment with the target. A counterweight is attached to the rotary frames to keep them in balance. The rotary frames are rotatably supported on rollers. The target on the treatment table is irradiated with the radiation beam while the rotary frames are being rotated by a rotational drive unit.

However, it is much more technically challenging, takes up a larger space, requires a more tedious and time-consuming accuracy control task, and is much more costly to construct a rotary gantry structure which incorporates an apparatus for applying a proton beam or a heavy ion beam than an apparatus for applying an X-ray. Even a proton beam or a heavy ion beam is not effective enough if applied to the patient in one direction only. Therefore, for better therapeutic results, it is desirable to be able to apply the particle beam at any desired angle for multiple-direction irradiation (multiple field irradiation). Furthermore, it is necessary that the particle beam be applied in highly accurate alignment with the position of the patient.

BRIEF SUMMARY OF THE INVENTION

An object of the present invention is to provide a particle beam irradiation system which includes a particle beam irradiation apparatus free of a rotary gantry structure, is capable of multiple field irradiation, has an overall simple structure, takes up a small space, is placed under easy accuracy control, can be manufactured at a low cost, and is capable of irradiating the affected area of a patient with a particle beam from many directions with high positional accuracy.

The present inventor has made intensive and extensive investigations in order to attain the above object. As a result of the investigations, it has been found out that, a particle beam irradiation system has a particle beam irradiation apparatus which is free of a rotating gantry structure and which irradiates a particle beam in one direction, and for irradiating the affected area of the patient with the particle beam, the patient rotates, so that the particle beam irradiation system can irradiate the particle beam from various direction, as in the case using the rotating gantry structure. For example, as conceptionally shown in FIG. 2, the irradiation direction of the irradiation apparatus 1 is fixed, the particle beam 1a is applied in one direction, preferably obliquely from a position above the human (the patient) 3 and the patient 3 is rotated, furthermore, for example, as conceptionally shown in FIGS. 3A through 3C, the patient fixing device 4 for fixing the patient (not shown in FIGS. 3A through 3C) is rotatable (tiltable) with respect to the floor surface (ground surface) G. With this construction, it is possible to change the irradiation angle of the particle beam 1a applied in one direction with respect to the affected area 3a of the patient (not shown in FIGS. 3A through 3C) fixed by the patient fixing device 4, so that it is capable of irradiating the affected area of the patient with the particle beam from many directions. Furthermore, for example, as shown in FIGS. 3A through 3C, the CT scanner 2 and the patient fixing device 4 are tiltable at the same angle with respect to the floor surface (ground surface) G, so that, as shown in FIG. 3B, when the patient fixing device 4 is in the state that is tilt with respect to the floor surface (ground surface) G, the patient fixing device 4 is inserted in the detection range 2a of CT scanner 2 at the tilt angle as is and the CT scanning is possible in the tilt state. The above object is attained by the construction in which the patient fixing device is rotated or moved so that it is possible to irradiate the affected area of the patient with the particle beam from many directions, by the patient fixing device which is movable between the particle beam irradiation apparatus and the CT scanner and the positionally confirming the affected area of the patient rotated or moved is possible.

According to an embodiment of the present invention, there is provided a particle beam irradiation system including: a particle beam irradiation apparatus having a particle beam irradiator for irradiating an affected area of a patient with a particle beam from one direction, the particle beam irradiation apparatus being free of a gantry structure, the particle beam irradiator being housed in a chamber; a CT scanner installed in the chamber, for positionally confirming the affected area of the patient; a drive unit for moving the patient from a detection range of the CT scanner to an irradiation range of the particle beam irradiation apparatus; a patient fixing device for fixing the patient in position, the patient fixing device being mounted on said drive unit for rotation about the craniocaudal axis of the patient; and a housing unit having a structure housing the drive unit with the patient fixing device mounted and the CT scanner, the housing unit being rotatable about an axis perpendicular to a plane including a direction in which the particle beam is applied by the particle beam irradiation apparatus and a direction in which the drive unit moves. Here, "a detection range of the CT scanner" means the central part (area, range) of the gantry of the CT scanner and "an irradiation range of the particle beam irradiation apparatus" means the part (area, range) which the particle beam passes in the treatment chamber.

With this configuration, it is possible to accurately confirm the position of the affected area of the patient with the CT scanner from any of various angles and irradiate an affected area from any of various angles by combining the rotary motion of the patient fixing device with movement of the drive unit and the rotary motion of the housing unit.

According to the particle beam irradiation system as justmentioned, preferably, the particle beam irradiation apparatus applies the particle beam obliquely to the affected area from a position above the affected area.

With this configuration, it is possible to set the patient's body to more comfortable posture (physique) while the patient fixing device is rotated (tilted) to allow the particle beam irradiation apparatus to apply the particle beam to the affected area of the patient from many directions.

According to the particle beam irradiation system as justmentioned, preferably, the direction in which the particle beam is applied by the particle beam irradiation apparatus, the axis about which the housing unit is rotatable, and the craniocaudal axis about which the patient fixing device is rotatable cross each other at the affected area of the patient when the affected area is irradiated with the particle beam.

With this configuration, it becomes easy to irradiate the affected area of the patient with a particle beam accurately even if the patient fixing device is rotated and when the CT scanner confirms the position of the affected area of the patient, the movement of the patient fixing device between the irradiation apparatus and the CT scanner becomes easy.

The above and other objects, features, and advantages of the present invention will become apparent from the following description when taken in conjunction with the accompanying drawings which illustrate a preferred embodiment of the present invention by way of example.

DETAILED DESCRIPTION OF THE INVENTION

Figure 1:
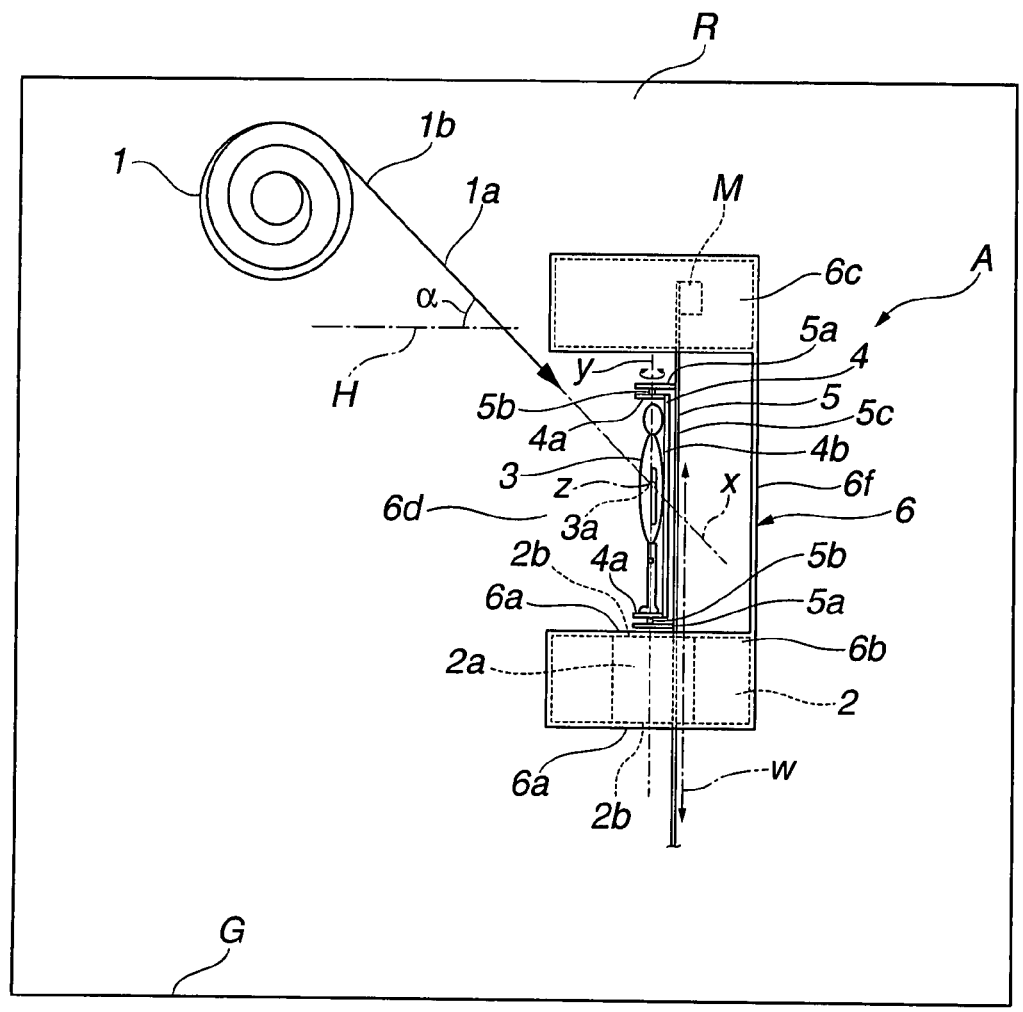
FIG. 1 is a schematic side elevational view of a particle beam irradiation system according to an embodiment of the present invention.

A particle beam irradiation system according to an embodiment of the present invention will be described in detail below with reference to the drawings. FIG. 1 shows in schematic side elevation the particle beam irradiation system according to an embodiment of the present invention. As shown in FIG. 1, the particle beam irradiation system, generally designated by A, is installed in a treatment chamber R and includes a particle beam irradiation apparatus 1, a CT scanner 2, a patient fixing device 4 for fixing a patient 4, a drive unit 5 for moving the patient fixing device 4 between an irradiation range of the particle beam irradiation apparatus 1 and a detection range 2a of the CT scanner 2, and a housing unit 6 storing therein the CT scanner 2 and the drive unit 5 with the patient fixing device 4 mounted thereon. The housing unit 6 has opposite side walls which are positioned on the sides of the housing unit 6 that are respectively closer to and remoter from the viewer of FIG. 1. For an easier understanding of the particle beam irradiation system A, these opposite side walls are omitted from illustration in FIG. 1.

The particle beam irradiation apparatus 1 may be a known particle beam irradiation apparatus insofar as it emits a particle beam 1a such as a proton beam, a heavy ion beam, or the like from one direction. For example, the particle beam irradiation apparatus 1 may be the charged particle beam generator having the ion source, the preaccelerator, and the synchrotron disclosed in Patent Document 1, or the particle beam irradiation apparatus having the particle beam circularly accelerating means, the beam transporting means, and the irradiation field forming means disclosed in Patent Document 3. The particle beam irradiation apparatus 1 is positioned such that it applies the particle beam 1a in one direction to an affected area 3a of a patient 3 fixed by the patient fixing device 4. Specifically, when the patient 3 fixed by the patient fixing device 4 is in an upstanding position as shown in FIG. 1, the direction x along which the particle beam 1a is applied to the patient 3 on the patient fixing device 4 should preferably be set such that the particle beam 1a is applied obliquely to the affected area 3a of the patient 3 from a position above the affected area 3a of the patient 3. An irradiation angle α at which the particle beam 1a is applied to the patient 3 with respect to the horizontal plane H should preferably be about 45° or more preferably in a range of 45°±30°. Depending on the size and type of the particle beam irradiation apparatus 1, the particle beam irradiation apparatus 1 as a whole may not be placed in the treatment chamber R, but at least a particle beam irradiator 1b of the particle beam irradiation apparatus 1 should be housed in the treatment chamber R.

The CT scanner 2 may include a known CT scanner. The CT scanner 2 is placed in an end of the housing unit 6. When the patient 3 is in the upstanding position shown in FIG. 1, the patient 3 placed on the patient fixing device 4 mounted on the drive unit 5 can be inserted in the detection range 2a of the CT scanner 2. Upon rotation of the housing unit 6, the CT scanner 2 can be angularly moved to any desired angular position and set to any desired angle between a horizontal position parallel to a floor surface (ground surface) G (see FIGS. 3A through 3C) and a vertical position perpendicular to the floor surface G, in unison with the drive unit 5 and an actuator M thereof.

The patient fixing device 4 with the patient 3 held thereby in a given posture is mounted on the drive unit 5. The patient fixing device 4 may be detachably mounted on the drive unit 5 or may be fixedly mounted on the drive unit 5. The patient fixing device 4 is mounted on the drive unit 5 such that it can be rotated about the craniocaudal axis y of the patient 3 and can be angularly set to a desired angle about the craniocaudal axis y. The patient fixing device 4 has a position adjusting function to adjust its position with respect to the drive unit 5 in the lateral and anteroposterior directions of the patient 3 for aligning the affected area 3a of the patient 3 into accurate alignment with the irradiated spot of the particle beam 1a. The patient fixing device 4 may not have a position adjusting function to adjust its position with respect to the drive unit 5 in the craniocaudal directions of the patient 3 because the patient fixing device 4 can be positionally adjusted in the craniocaudal directions upon movement of the drive unit 5.

The patient fixing device 4 has a pair of opposite bases 4a and a fixing plate 4b for fixing the patient 3 while holding the patient 3 in a given posture. The patient fixing device 4 can be moved with the drive unit 5 in the craniocaudal directions of the patient 3 placed on the patient fixing device 4. The patient fixing device 4 is mounted on the drive unit 5 for rotation about the craniocaudal axis y of the patient 3 independently of the drive unit 5. The patient fixing device 4 may be rotated by any of various means. According to the illustrated embodiment, two support bases 5a, which may be spaced about 2 m from each other in the vertical direction in FIG. 1 for accommodating various body heights therebetween, are secured to the drive unit 5 in a region thereof where the patient is to be placed, and the bases 4a of the patient fixing device 4 are rotatably connected to the respective support bases 5a by respective pivot shafts 5b. A stop, not shown, is provided between the patient fixing device 4 and the drive unit 5 for locking the patient fixing device 4 in a desired angular position with respect to the drive unit 5. Alternatively, the base 4a of the patient fixing device 4 which is positioned at the feet of the patient 3 on the patient fixing device 4 may be rotated as a turntable by an actuator, not shown, and the rotated base 4a may be locked in a desired angular position by a locking unit, not shown. The patient fixing device 4 may be rotated either by the drive unit 5 or manually. Further alternatively, a base 4a, a support base 5a, and a pivot shaft 5b may be provided only at the feet of the patient 3. When in actual use, the patient fixing device 4 may not be rotated through 360°, but may be controlled to make pendular motion with an amplitude selected for a better particle beam dose. Though the patient fixing device 4 may be made of any of various materials, it should preferably be made of a radiation-permeable material such as fiber-reinforced plastics, for example. The patient 3 may be fastened to the patient fixing device 4 by a fastening member such as a band, not shown.

As described above, the patient fixing device 4 has a position adjusting function to adjust its position with respect to the drive unit 5 in the lateral and anteroposterior directions of the patient 3 for aligning the affected area 3a of the patient 3 into accurate alignment with the irradiated spot of the particle beam 1a. The position adjusting function may be provided as follows: The support bases 5a have a plurality of holes (not shown) defined therein in a position adjustable range, and after the pivot shafts 5b are inserted in selected ones of the holes in the support bases 5a, the pivot shafts 5b are secured to the support bases 5a, thereby positionally adjusting the patient 3 in the lateral and anteroposterior directions thereof. The craniocaudal axis y of the patient 3 about which the patient fixing device 4 is rotatable should extend through the affected area 3a of the patient 3. In view of the thickness of the body of the patient 3, the fixing plate 4b of the patient fixing device 4 should preferably be positionally adjustable with respect to the rotational axis provided by the pivot shafts 5b in order to allow the particle beam irradiation apparatus 1 to accurately irradiate various affected areas, such as tumors, of patients 3. For example, the fixing plate 4b may be slidably attached to the bases 4a to positionally adjust the patient 3 such that the rotational axis provided by the pivot shafts 5b passes through the affected area 3a of the patient 3 fixed to the fixing plate 4b. Alternatively, the bases 4a may have a plurality of holes (not shown) defined therein in a position adjustable range, and the pivot shafts 5b are inserted in selected ones of the holes in the bases 4a in alignment with the affected area 3a of the patient 3 secured to the fixing plate 4b, so that the bases 4a are rotatable about the pivot shafts 5b.

The drive unit 5 serves to move the patient fixing device 4 between the irradiation range of the particle beam irradiation apparatus 1 and the detection range 2a of the CT scanner 2, as described above. In the illustrated embodiment, the drive unit 5 is housed in the housing unit 6 such that it has a front end (upper end in FIG. 1) disposed in a housing chamber 6c of the housing unit 6 and a rear end (lower end in FIG. 1) extending through the detection range 2a of the CT scanner 2 that is housed in a CT scanner housing chamber 6b of the housing unit 6. The drive unit 5 can be angularly moved to any desired angular position and set to any desired angle between the horizontal position parallel to the floor surface (ground surface) G (see FIGS. 3A through 3C) and the vertical position perpendicular to the floor surface G, in unison with the CT scanner 2. The drive unit 5 may be attached to the housing unit 6 by any of various means. For example, the drive unit 5 is coupled to the actuator M which is securely installed in the housing chamber 6c of the housing unit 6, so that the drive unit 5 is connected to the housing unit 6. As described above, the patient fixing device 4 is rotatably mounted on the drive unit 5 for rotation about the craniocaudal axis y of the patient 3. The patient fixing device 4, the CT scanner 2, and the drive unit 5 can be rotated and tilted about an axis z, which extends perpendicularly to the sheet of FIG. 1, for pendular motion in unison with each other.

The drive unit 5 has an actuating means for moving the patient 3 secured to the patient fixing device 4. The actuating means is not limited to any actuating means, but may be of any of various means insofar as it can smoothly move the patient 3 secured to the patient fixing device 4. For example, the actuating means has a plate-line planar structure on which the patient fixing device 4 is mounted. The actuating means moves, with the actuator M through gears, not shown, the affected area 3a of the patient 3 accurately from an image-capturing position (the detection range 2a) of the CT scanner 2 to an irradiation position (the irradiation range) of the particle beam irradiation apparatus 1. The plate-like planar structure of the actuating means on which the patient fixing device 4 is mounted at a position 5c may be made of a material which does not obstruct the image-capturing operation of the CT scanner 2. For example, the plate-like planar structure may be made of fiber-reinforced plastics, carbon fiber, or the like. Since the affected area 3a of the patient 3 may be located anywhere in the patient 3, e.g., the head or a lower leg, the drive unit 5 should be able to move the patient fixing device 4 over a distance preferably ranging from 1 m to 10 m or more preferably ranging from 2 m to 5 m.

The housing unit 6 is of a structure housing therein at least the drive unit 5 with the patient fixing device 4 mounted thereon and the CT scanner 2. According to the illustrated embodiment, as shown in FIG. 1, the CT scanner housing chamber 6b, which is disposed in an end (lower end in FIG. 1) of the housing unit 6, houses the CT scanner 2 immovably therein. The CT scanner housing chamber 6b has a pair of openings 6a defined respectively in opposite side walls (upper and lower side walls in FIG. 1) aligned with respective openings 2b defined in respective opposite side walls (upper and lower side walls in FIG. 1) of the CT scanner 2. The housing chamber 6c, which is disposed in an opposite end (upper end in FIG. 1) of the housing unit 6, houses therein the actuator M for moving the patient 3 placed on the patient fixing device 4 along the craniocaudal axis y. The housing chamber 6c also houses therein a counterbalance, not shown, which together with the actuator M balances the CT scanner 2. The housing unit 6 has an irradiation cavity 6d defined between the CT scanning housing chamber 6b and the housing chamber 6c and open toward the particle beam irradiation apparatus 1 for allowing the particle beam irradiation apparatus 1 to apply the particle beam 1a directly to the affected area 3a of the patient 3 placed on the patient fixing device 4. When the particle beam irradiation apparatus 1 is in operation to apply the particle beam 1a, the patient fixing device 4 mounted on the drive unit 5 is disposed in the irradiation cavity 6d between the CT scanning housing chamber 6b and the housing chamber 6c. The housing unit 6 may be of any structure for housing therein at least the drive unit 5 with the patient fixing device 4 mounted thereon and the CT scanner 2. Rather than being housed in the CT scanner housing chamber 6b, the CT scanner 2 may directly be housed in the housing unit 6 such that the CT scanner 2 may have walls (upper and right walls in FIG. 1) fixed to a rear wall 6f of the housing unit 6 (a wall confronting the irradiation opening 6d).

The housing unit 6 is rotatable about the axis z which extends perpendicularly to a plane (lying in the sheet of FIG. 1) which includes both the direction x in which the particle beam 1a is applied and the direction w which the drive unit 5 moves. If the particle beam 1a is applied obliquely to the affected area 3a of the patient 3 from a position above the affected area 3a as shown in FIG. 1, then the axis z may be referred to as a horizontal axis (extending toward and away from the viewer of FIG. 1) perpendicular to the direction x along which the particle beam 1a is applied to the patient 3. The axis z is set so as to extend through the affected area 3a of the patient 3 placed on the patient fixing device 4. By positionally adjusting the patient 3 so that the direction x in which the particle beam 1a is applied crosses the affected area 3a of the patient 3 placed on the patient fixing device 4 and the craniocaudal axis y of the patient 3, about which the patient fixing device 4 is rotatable, passes through the affected area 3a of the patient 3 placed on the patient fixing device 4, the direction x in which the particle beam 1a is applied, the craniocaudal axis y of the patient 3, and the axis z about which the housing unit 6 is rotatable cross each other at the affected area 3a of the patient 3 when it is irradiated with the particle beam 1a.

Figure 4:
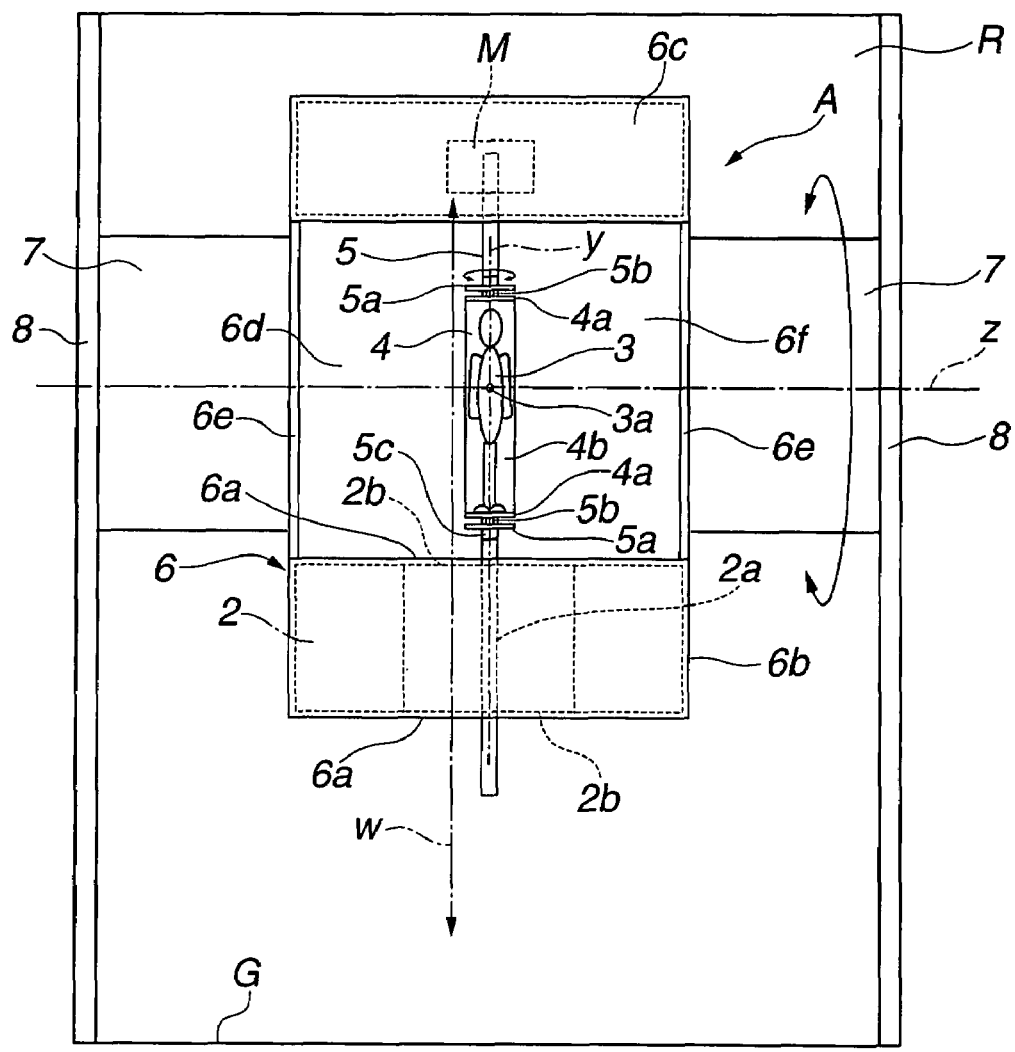
FIG. 4 is a front elevational view of the particle beam irradiation system.

The housing unit 6 may be made rotatable by any of various means. For example, as shown in FIG. 4, opposite side walls 6e of the housing unit 6 are rotatably supported on respective opposite side walls 8 of the treatment chamber R (irradiation chamber) by respective shafts 7, so that the housing unit 6 is suspended so as to be tiltable (rotatable) with respect to the floor surface (ground surface) G, and the shafts 7 have their central axes aligned with the axis z. The housing unit 6 may be rotated or tilted for pendular motion with respect to the floor surface (ground surface) G by any of various rotating mechanisms. For example, a combination of rotational components such as gears and an actuator such as a motor may be used as such a rotating mechanism. The rotating mechanisms and the moving mechanisms employed in the present embodiment should preferably be controllable by a computer and should also preferably be manually adjustable. The housing unit 6 may be made of any of various materials insofar as it is strong enough to house the CT scanner 2 therein and withstand rotation of the housing unit 6. The shafts 7 are made of a material strong enough, and have a diameter large enough, to support the housing unit 6 in suspension and allow the housing unit 6 to rotate. The shafts 7 should preferably be adjustable in height and position with respect to the housing unit 6. For allowing the particle beam irradiation apparatus 1 to treat various affected areas in different positions ranging from a tumor in the head to tumors in the lower part of the body of the patient, e.g., the prostate and the large intestine, the housing unit 6 should desirably be of such a height as to allow the lower part of the body of the patient in an upstanding posture to be irradiated with the particle beam 1a and inspected by the CT scanner 2.

Figure 3A:
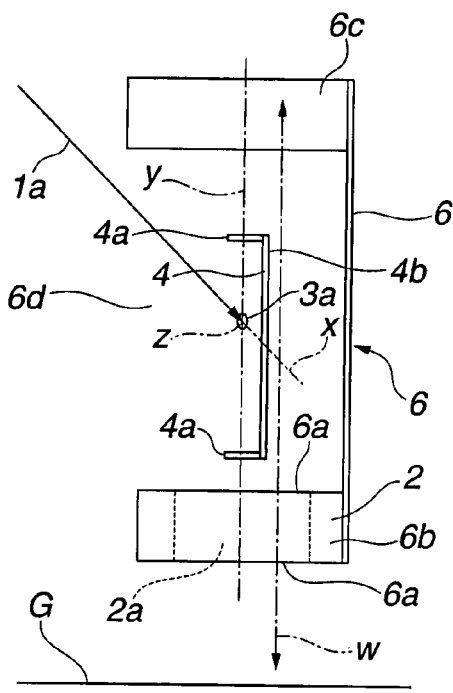
FIGS. 3A through 3C are schematic side elevational views illustrative of another mode of axis rotation of the particle beam irradiation system.
Figure 3B:
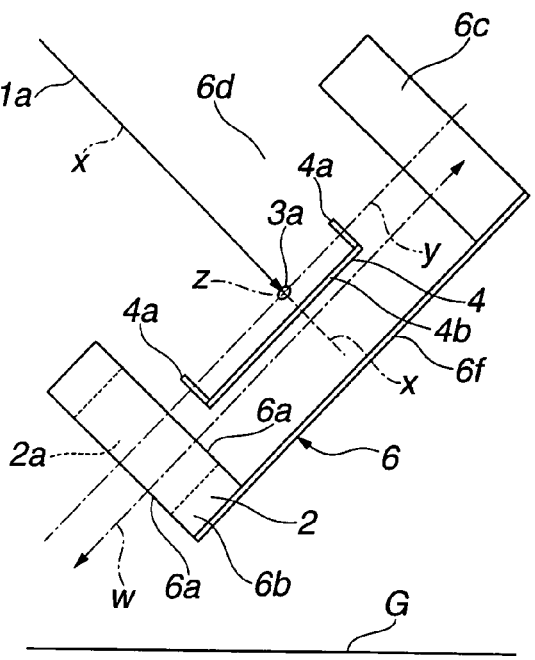
Figure 3C:
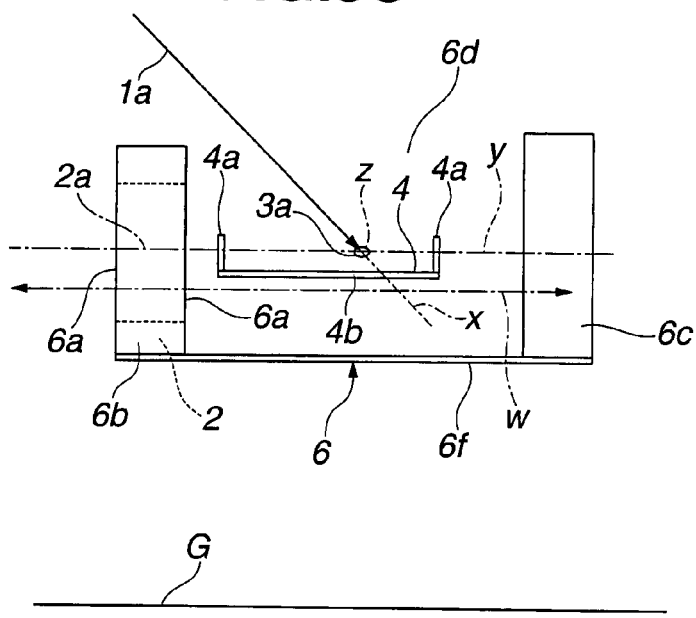

The housing unit 6 is angularly movable about the axis of the shafts 7 to allow the housing unit 6 which houses the CT scanner 2, the drive unit 5 with the patient fixing device 4 mounted thereon, and the actuator M to be set to any of various angles with respect to the particle beam 1a, as shown in FIGS. 3A through 3C. The housing unit 6 may be angularly moved through any angle suitable for giving a better radiation dose distribution to the patient 3 placed on the patient fixing device 4 that is mounted on the drive unit 5. Preferably, as shown in FIGS. 3A through 3C, the housing unit 6 should be angularly movable in an angular range from 0° to 90° with respect to the floor surface (ground surface) G, i.e., in an angular range from the angular position shown in FIG. 3A to the angular position shown in FIG. 3C. In FIGS. 3A through 3C, the opposite side walls of the housing unit 6 are omitted from illustration. In order to permit the housing unit 6 to rotate smoothly about the axis z, the weights of the CT scanner 2 and the actuator M combined with the counterbalance should be held in equilibrium, as described above.

The particle beam irradiation system A operates as follows: First, the particle beam irradiation system A is set to have the central axis of the particle beam 1a positioned in exact alignment with a transversely central area of the drive unit 5. Then, the patient fixing device 4 is positionally adjusted to position the affected area 3a of the patient 3 substantially in alignment with the transversely central area of the drive unit 5. Thereafter, the drive unit 5 is actuated to bring the affected area 3a into the detection range 2a of the CT scanner 2. After the CT scanner 2 has inspected the affected area 3a to confirm the position of the affected area 3a, the patient fixing device 4 is positionally adjusted in the lateral and anteroposterior directions of the patient 3 with respect to the drive unit 5 to accurately keep the affected area 3a in alignment with the transversely central area of the drive unit 5. Thereafter, the drive unit 5 is actuated to aim the irradiated spot of the particle beam 1a at the affected area 3a. Then, the particle beam irradiation apparatus 1 is energized to irradiate the affected area 3a with the particle beam 1a. The above process represents a basic therapeutic process performed by the particle beam irradiation system A.

Figure 2:
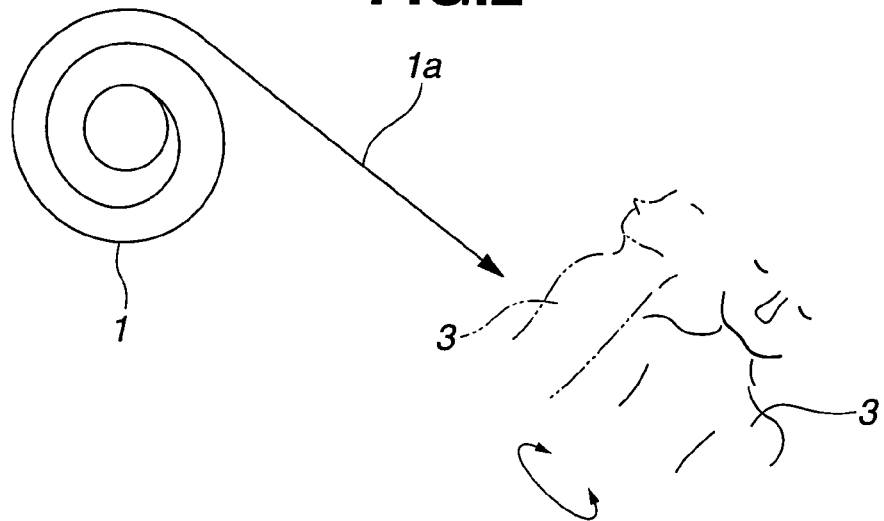
FIG. 2 is a schematic view illustrative of a mode of axis rotation of the particle beam irradiation system.

In the therapeutic process performed by the particle beam irradiation system A, the patient fixing device 4 is rotated about the craniocaudal axis y of the patient 3 to aim the particle beam 1a not only at a front side of the patient 3, but also at either lateral side of the patient 3, as shown in FIG. 2, and the housing unit 6 is rotated about the axis z to aim the particle beam 1a at the affected area 3a in a wide craniocaudal range. These rotary motions of the patient fixing device 4 and the housing unit 6 may be combined with each other to allow the particle beam irradiation apparatus 1 to apply the particle beam 1a to the affected area 3a from various directions in a three-dimensional space.

According to the particle beam irradiation system A, the patient 3 placed on the patient fixing device 4 can be rotated about two axes, and the particle beam 1a emitted from the particle beam irradiation apparatus 1 can be applied in multiple field irradiation without the need for a rotary gantry structure to be incorporated into the particle beam irradiation apparatus 1. When the patient 3 is rotated, the position of the patient 3 can be confirmed again by the CT scanner 2 and then the patient 3 can be irradiated with the particle beam 1a. Therefore, the patient 3 can be irradiated with the particle beam 1a with high positional accuracy for excellent therapeutic outcomes.

Although a certain preferred embodiment of the present invention has been shown and described in detail, it should be understood that various changes and modifications may be made therein without departing from the scope of the appended claims.

What is claimed is:

1. A particle beam irradiation system comprising:
   a particle beam irradiation apparatus having a particle beam irradiator for irradiating an affected area of a patient with a particle beam from one direction, said particle beam irradiation apparatus being free of a gantry structure, said particle beam irradiator being housed in a chamber;
   a CT scanner installed in said chamber, for positionally confirming said affected area of the patient;
   a drive unit operable to move said patient between a detection zone of said CT scanner and an irradiation zone of said particle beam irradiation apparatus;
   a patient fixing device for fixing said patient in position, said patient fixing device being mounted on said drive unit, and being rotatable about the craniocaudal axis of said patient; and
   a housing unit having a structure carrying said drive unit with said patient fixing device mounted and said CT scanner, said housing unit being rotatable in said chamber about an axis perpendicular to a plane including a direction in which the particle beam is applied by said particle beam irradiation apparatus and a direction in which said drive unit moves.

2. A particle beam irradiation system according to claim 1, wherein the direction in which the particle beam is applied by said particle beam irradiation apparatus, said axis about which said housing unit is rotatable, and said craniocaudal axis about which said patient fixing device is rotatable cross each other at said affected area of the patient when said affected area is irradiated with the particle beam.

3. A particle beam irradiation system according to claim 1, wherein said housing unit is rotatable in said chamber about a horizontal axis.

4. A particle beam irradiation system according to claim 1, wherein said patient fixing device comprises a position adjusting function to adjust its position with respect to said drive unit in the lateral and anteroposterior directions of said patient.

5. A particle beam irradiation system according to claim 1, wherein said patient fixing device is mounted on said drive unit such that it can be rotated about the craniocaudal axis of said patient independently of said operation of the drive unit.

6. A particle beam irradiation system according to claim 1, wherein opposite side walls of said housing unit are rotatably supported on respective opposite side walls of said chamber by respective shafts to suspend said housing unit in said chamber.

7. A particle beam irradiation system according to claim 1, wherein the patient fixing device and the CT scanner are tiltable at a same angle with respect to a floor surface.

8. A particle beam irradiation system according to claim 1, wherein said housing unit is rotatable in said chamber about the axis perpendicular to the plane including a direction in which the particle beam is applied by said particle beam irradiation apparatus and a direction in which said drive unit moves, so that the irradiation angle of the particle beam applied in one direction is changed with respect to the affected area of the patient, to irradiate the affected area of the patient with the particle beam from a plurality of directions at a plurality of angles.

9. A particle beam irradiation system according to claim 1, wherein the patient's body is set to various angles by said fixing device and said housing unit.

10. A particle beam irradiation system according to claim 1, wherein said particle beam irradiation apparatus is positioned relative to the housing unit so as to direct the particle beam obliquely onto said affected area from above.

11. A particle beam irradiation system according to claim 10, wherein an irradiation angle at which said particle beam is applied to said patient with respect to a horizontal plane is in a range of 45°±30°.

12. A particle beam irradiation system according to claim 1, wherein said drive unit comprises an actuating unit for moving said patient fixing device with said patient secured thereto, wherein said actuating unit comprises a plate-line planar structure on which said patient fixing device is mounted, and said actuating unit is operable by an actuator through gears to move said affected area of said patient between said detection zone of said CT scanner and said irradiation zone of said particle beam irradiation apparatus.

13. A particle beam irradiation system according to claim 12, wherein said housing unit houses therein a counterbalance which together with said actuator balances said CT scanner.

* * * * *